United States Patent [19]

Hermann, Jr. et al.

[11] Patent Number: 4,892,525
[45] Date of Patent: Jan. 9, 1990

[54] HYPODERMIC NEEDLE PROTECTIVE BARREL AND CAP PACKAGING

[75] Inventors: William J. Hermann, Jr., Sealy; John R. Zanek, Missouri City, both of Tex.

[73] Assignee: Synertex, Missouri City, Tex.

[21] Appl. No.: 571,779

[22] Filed: Jan. 18, 1984

[51] Int. Cl.$^4$ .............................................. A61M 5/32
[52] U.S. Cl. ..................... 604/263; 604/192; 206/365; 206/438
[58] Field of Search ............... 604/192–199, 604/263; 206/364, 365, 438

[56] References Cited

U.S. PATENT DOCUMENTS

| | | | |
|---|---|---|---|
| 2,953,243 | 9/1960 | Roehr | 604/263 |
| 3,021,942 | 2/1962 | Hamilton | 206/43 |
| 3,107,785 | 10/1963 | Roehr | 206/63.2 |
| 3,149,717 | 9/1964 | Castelli | 206/43 |
| 3,245,567 | 4/1966 | Knight | 604/263 |
| 3,329,146 | 7/1967 | Waldman | 128/221 |
| 3,333,682 | 8/1967 | Burke | 206/43 |
| 3,344,787 | 10/1967 | MacLean | 128/221 |
| 3,677,247 | 7/1972 | Brown | 604/197 |
| 3,865,236 | 2/1975 | Rycroft | 206/364 |
| 4,091,811 | 5/1978 | Bates et al. | 604/263 |
| 4,237,882 | 12/1980 | Wickham | 128/218 N |
| 4,240,427 | 12/1980 | Akhavi | 128/218 N |
| 4,248,246 | 2/1981 | Ikeda | 604/263 |
| 4,300,678 | 11/1981 | Gyure et al. | 604/263 |
| 4,419,098 | 12/1983 | Bennett | 604/263 |
| 4,435,177 | 3/1984 | Kuhlemann et al. | 604/263 |

FOREIGN PATENT DOCUMENTS 221221  5/1962  Austria .............................. 604/263

*Primary Examiner*—John F. Niebling
*Assistant Examiner*—Kathryn Gorgus
*Attorney, Agent, or Firm*—Fitzpatrick, Cella, Harper & Scinto

[57] ABSTRACT

The present invention relates to improvements in conventional protection barrel and cap packagings for hypodermic needles, whereby a structural guard is provided to encourage a user's fingers to locate directly behind the guard, and around the outer surface of an opening into the protected barrel. A person inserting a needle into a barrel automatically seeks to grasp the barrel proximate its open end, to avoid yawing of the barrel during the manipulative process. The present invention facilitates holding of a barrel proximate the opening, while providing, as an extension therefrom, a needle entrance guide means which extends axially and laterally therefrom. The laterally expanded barrel opening defines a transition ramp surface into the barrel open end. Accordingly, the present invention ensures that the needle will be guided into the barrel open end and towards the barrel closed end, even if the needle insertion step included an initial lateral misalignment, off the axial centerline of the barrel cap which extends the guard protections of the barrel needle barrel protector, through a cap which comprises an extending boss from the exterior surface of the cap, so that both needles will be guided away from accidental, manipulative stabbing.

A fourth object of the present invention is to provide a protective barrel and extended cap packaging for enclosing a hypodermic needle and syringe assembly, wherein a disposable axially extending housing can be discarded, leaving a protective needle barrel to offer protection to the user, when reinserting only the barrel onto the needle.

14 Claims, 2 Drawing Sheets

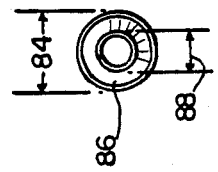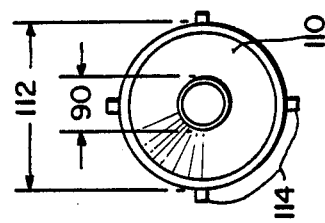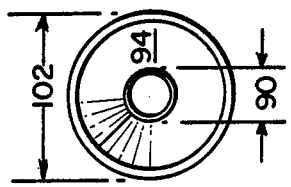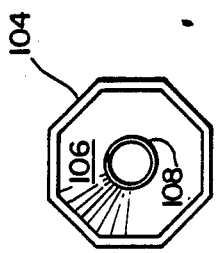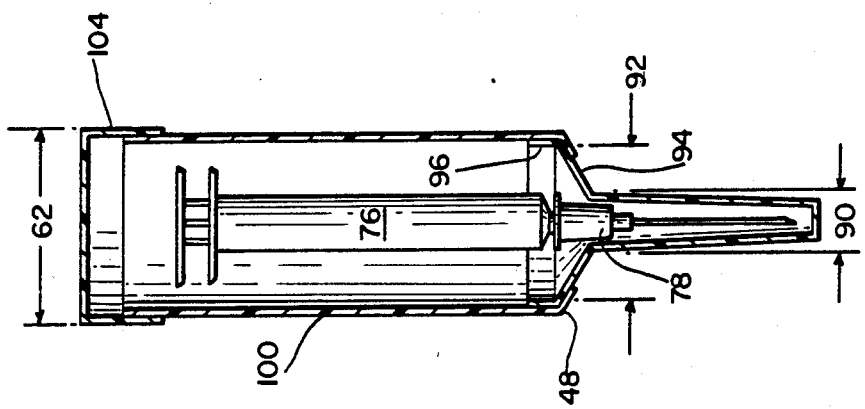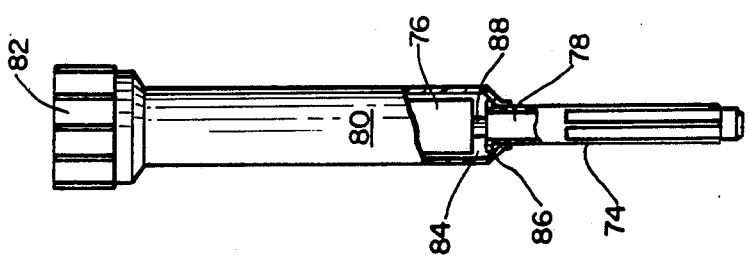

HYPODERMIC NEEDLE PROTECTIVE BARREL AND CAP PACKAGING

BACKGROUND OF THE INVENTION

1. Field of the Invention

The present invention relates to improvements in packaging for enclosing a hypodermic needle, and a hypodermic needle and syringe combination. The packaging maintains sterility and reduces the likelihood or injury to the manipulator, when placing the needle or syringe/needle combination in its protective guard, after use.

2. Brief Description of the Prior Art

Various prior packaging designs have been configured upon the concept of facilitating a manipulation of a needle or a syringe/needle combination into, or out of, a protective sterile packaging. Prior art techniques known to Applicant are represented by the U.S. patents, as follows:

ROEHR, 3,107,785
HAMILTON, 3,021,942
CASTELLI, 3,149,717
WALDMAN, Jr. 3,329,146
BURKE, 3,333,682
MacLEAN, 3,344,787
RYCROFT, 3,865,236
WICKHAM, 4,237,882
AKHAVI, 4,240,427

In summary, while certain of these patents illustrate needle packages having flanged entrance designs, there is not found a teaching which suggests that a widely divergent cap and protector barrel design might be employed, completely to cover the exposed forefinger and thumb area of a user when replacing the cap or barrel.

The listed patents primarily illustrate different techniques for protecting sterility of a needle, while facilitating attachment of the needle to a syringe. MacLEAN and HAMILTON specifically note that the problem of accidental stabbing exists; however, both HAMILTON (column 1, lines 15-70) and MacLEAN focus upon a stabbing during the step of attaching the needle to the syringe, and do not address the more serious problem of stabbing when subsequently inserting a protective barrel over the needle, after use.

ROEHR and BURKE illustrate typical, narrow barrels for needles which require very accurate axial manipulation of a needle, to ensure a resinsertation without a finger stab.

The art appears to have focused upon improving techniques for threading a needle hub onto a collar, while facilitating alignments. The 1962 flange teachings of HAMILTON do not provide finger protection when the barrel is grabbed about barrel surface 15. Similarly, the Baxter Labs patent in the name of WALDMAN focuses upon an improved facility for a wrenching action, to manipulate a hub interlock.

The 1967 teachings in the patent to MacLEAN incidentally illustrate the common extent of lateral finger exposure, in a patent concerned with a needle mounting hub, having columns of separate threads, better to enable a tightening.

The most recent patents illustrate continuing interest in providing a protective barrel which acts as a wrench, and manufacturing enhancements for various interconnect thread designs. The Becton and Dickinson patent in the name of RYCROFT, also shows a check valve, to facilitate sealing of the needle from the atmosphere. The Sherwood Medical Industries patent, in the name of WICKHAM, shows a separate syringe barrel extension and barrel needle connector, of the type reproduced herein at FIG. 7. The American Hospital Supply patent in the name of AKHAVI emphasizes a beveling technique on a needle hub, to facilitate high-speed manufacture of such assemblies, without locking up the needle hub against an otherwise conventional protector barrel threads.

In summary, known syringe and needle protector barrel designs appear to focus upon interlock structures to enable a more accurate and positive connection of the needle to the syringe, while maintaining the sterility between the protector barrel and the needle. The present invention addresses an entirely different problem; accidental stabbing when the needle protector is being replaced over the needle, after use. The prior art does not suggest a axially flanged, funnel-shaped entrance guide means projecting upwardly from the barrel, to act as a guard for the operator's fingers; which invariably will surround the entrance end of a protective barrel during needle reinsertion.

SUMMARY OF THE INVENTION

A first object of the present invention is to provide a protective barrel and cap packaging which will ensure that the operator's fingers are substantially protected against axially misalignments, when the operator is replacing the needle into the protective barrel, prior to a reuse or disposal, for example. The present invention recognizes the fact that any protective device must inherently assist the user against an accidental finger stab with a used needle. Hospital personnel invariably are under stress when dealing with procedures requiring use of a needle and syringe. The first object of the invention is achieved by a structure which provides a natural position for grasping a needle protective barrel, and a natural position which protects fingers from an axially misaligned needle stabbing.

A second object of the present invention is to provide a protective barrel and cap packaging which will include an entrance guide means with a ramp surface, to guide a misaligned needle tip into the open end of a barrel, and still allow for a finger grasping of the needle hub, should it be necessary to remove the hub from the packaging.

The third object of the present invention is to provide a protective barrel and cap packaging for enclosing a hypodermic needle, of the type used with multi-sample blood sample collection procedures, wherein a multi-sample tube has a projecting needle extending from either end of a hub assembly. This third object of the invention is accomplished by a protective cap which extends the guard protections of the barrel needle barrel protector, through a cap which comprises an extending boss from the exterior surface of the cap, so that both needles will be guided away from accidental, manipulative stabbing.

A fourth object of the present invention is to provide a protective barrel and extended cap packaging for enclosing a hypodermic needle and syringe assembly, wherein a disposable axially extending housing can be discarded, leaving a protective needle barrel to offer protection to the user, when reinserting only the barrel onto the needle.

The present invention generally comprises improvements to conventional protective barrel and cap packagings for enclosing a hypodermic needle, wherein the structural guard provided has an inclined, obverse ramp surface which encourages a user's fingers to locate directly behind the guard, and around the outer surface of the opening into the protected barrel. A person inserting a needle into a barrel automatically seeks to grasp the barrel proximate its open end, to avoid yawing of the barrel during the manipulative process. The present invention facilitates holding of a barrel proximate the opening, while providing, as an extension therefrom, a needle entrance guide means which extends axially and laterally therefrom. The laterally expanded barrel opening defines a transition ramp surface into the barrel open end. Accordingly, the present invention ensures that the needle will be guided into the barrel open end and towards the barrel closed end, even if the needle insertion step included an initial lateral misalignment, off the axial centerline of the barrel. The barrel open end of the present invention is equivalent to these of prior art devices, in that a needle is held by a rational engagement, about an outer surface of the needle hub. The type of frictional engagement between hub and inner surface of the open end of the barrel and forms no part of the present invention, since any form of thread or cam action between the barrel and the hub will work, within the principles of the present invention.

In a preferred embodiment, the entrance guide means is circular along any lateral section, and a ramp surface is defined at an angle greater than 45 degrees, between its inner surface and the barrel centerline; creating a ramp which is funnel-shaped. The preferred environment also comprises a barrel and entrance guide means as a single, thin-wall structure, with a sharp transition between the ramp inner surface and the open end of the protective barrel. Also, and importantly, obverse to that ramp surface an outer surface to the entrance guide means then defines, in lateral projection, an annulus about the open end of the barrel. This annulus has a lateral, projected width preferably between 0.5 cm. and 1.5 cm. For example, if the outer dimension of the barrel open end is 1 cm., the present invention contemplates an entrance guide with an overall diameter of between 2 and 4 centimeters, so that the width of the annulus around the barrel open end would be between 0.5 cm. and 1.5 cm. Such a lateral projected width provides a zone, anywhere around the exterior of the barrel, considered substantially able to act as a guard for a finger which will be grasping the barrel about its open end. Since the obverse surface to a ramp surface of a thin-wall construction also will be inclined, an attempt by an operator to grasp the obverse surface to the guide ramp will result in his fingers sliding laterally towards a rest position on the outer surface of the barrel, just below the guide ramp and proximate the opening of the barrel. In the preferred embodiment, the funnel-shaped guide has its proximate or narrow end attached to the barrel opening and a distal end which further includes a small range extending axially from the ramp surface. This flange provides a surface against which a sealing can be accomplished, either by a one-piece protective cap, or a two-piece protective cap, which includes a right-circular cylinder extension, and a removable cap element thereupon. A two-piece cap facilitates enclosing an entire syringe and needle assembly within a protective packaging.

The preferred embodiment further comprises a double-form of protection for the user, in those instances where it is necessary to replace a cap over a barrel, into which a double needle has been inserted. The protective cap may include an enlarged open section, with a second ramp surface and an obverse surface which extends down to an extending boss, axially located with respect to the centerline of the cap. The external surface of the boss acts as a natural finger grasping location and also allows double, or multi-sample needle assembly to be inserted back into its protective packaging, with minimization of stabbing danger from either of the two needles. The angle of the second ramp surface is also calculated at greater than 45 degrees to the cap centerline, to ensure that a finger will not rest against the ramp surface during a manipulation. The boss may also have ridges, to facilitate grasping of the cap.

In a first embodiment of the present invention a single ramp protective barrel is employed, and any form of protective cap may be employed, provided the cap is sufficiently enlarged to engage with the extended opening area of the entrance guide means and ensure a protective seal. In a second embodiment of the invention, the cap includes a right-cylinder extension, which is configured with an inwardly directing flange on its proximate end, to engage against an outer portion of the obverse surface to the entrance guide means. This engagement provides a seal and enables removal of the barrel guard, out of the distal end of the right circular extension, in a conventional manner, while leaving the improved barrel in place on the needle.

For any of the embodiments, design options comprise a noncircular entrance guide means and non-roll surface projections. For example, a multi-faceted flange may be employed upon a ramp either of funnel or segmented geometric shape, or projections may be provided about the outer surface of the cap, to discourage rolling of the device upon a surface.

Further objects, features and advantages of the invention will become more apparent by considering the following embodiments of the invention, wherein reference is made to the accompanying drawings.

BRIEF DESCRIPTION OF THE DRAWINGS

FIG. 7 is a vertical elevation view, in partial section, showing a prior art device;

FIG. 8 is a vertical elevation view, in partial section, of a third embodiment of the present invention;

FIG. 9 is a top plan view of FIG. 7;

FIG. 10 is a top plan view of FIG. 8;

FIG. 11 is a top plan view of a fourth embodiment of the present invention; and, FIG. 12 is a top plan view of a fifth embodiment of the present invention.

DESCRIPTION OF THE PREFERRED EMBODIMENTS

Figure 1:
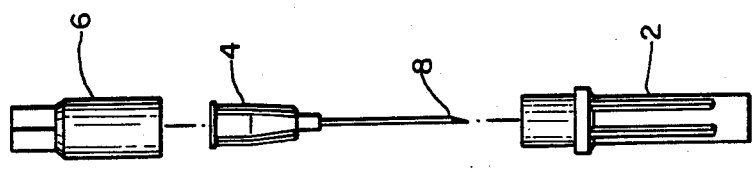
FIG. 1 is an explosion, elevation view of a first prior art packaging design, comprising a protective barrel, a needle with hub assembly, and a protective cap.

FIG. 1 illustrates a first prior art protective packaging for enclosing a hypodermic needle, where the combination essentially comprises a protective barrel, a needle hub, 4, from which a needle extends to a distal end, B, and a superposed protective cap, 6. FIG. 1 is roughly representational of packaging for the monoject, ®21X1", as available from Sherwood Medical Laboratories.

Figure 3:
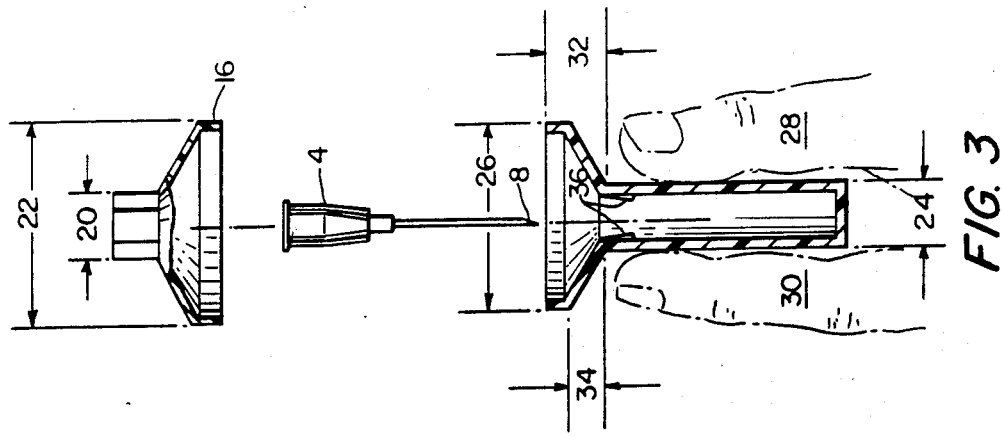
FIG. 3 is a explosion view of the embodiment of FIG. 2.
Figure 2:
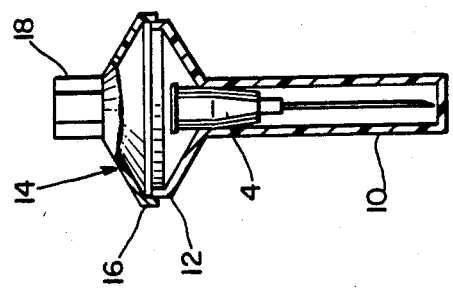
FIG. 2 is a front elevation view, in partial section, showing a first embodiment of the present invention.

FIGS. 2 and 3 represent a first embodiment of the present invention, wherein a protective barrel, 10, is substantially equivalent in length and width to the prior art protective barrel, 2, with the improvement of a needle entrance guide means, 12, attached to said barrel open end and extending both laterally and axially to define a transition ramp surface. The ramp surface is defined on the interior of the entrance guide means and has dimensions configured for two purposes. As shown in FIG. 3, the overall width of the entrance guide means, 26, is illustrated to be substantially greater than the overall width of the outer surface of the barrel open end, 24. A user's forefinger, 30, and thumb, 28, are shown grasping about the barrel opening area, which includes, at its open end, any form of frictional engagement device, as shown schematically at 36. The entrance guide means has an overall axial extension, 32, (including a small axial flange), and an axial extension, 34, defined as the axial extension for the ramp surface. An annulus is defined between the outer dimension of the entrance guide means, 26, and the outer surface of the barrel, 24, with this guide means, forward of the tips of finger 30, and thumb, 28. The angle of the ramp surface structurally is defined by the dimension 34 and half of the difference, between the overall width, 26, and the barrel width, 24. For purposes of the present invention, the angle of the inclined ramp surface defined must accomplish two objectives. First, it must be sufficient to define an annulus having a width capable of substantially protecting a finger at any circumferential position about the outer surface of the barrel while providing the aforementioned natural grasping position, around the barrel proximate to the actual opening of the barrel, at 36. Second, the ramp must be sufficiently inclined, away from the centerline of the device, so as to enable a finger to grasp the top of the needle hub, 4, when a needle is within the barrel, as shown in the position of FIG. 2. It should be appreciated that in the FIG. 1 prior art device, the hub, 4, remains exposed, above the structure of the barrel cap, 2. According to the present invention, an operator will be able to manipulate the needle hub, 4, without significant interference from the inclined ramp surface of the entrance guide means, 12. In the preferred embodiment of FIGS. 2 and 3, the dimension 34 is approximately 0.7 cm. thereby defining an angle between the inner ramp surface and the centerline of the device which is greater than 45 degrees, and preferably 50–80 degrees.

As shown most graphically in FIG. 3, when compared to FIG. 1, insertion of the needle hub, 4, will involve a target area, 26, which substantially is greater in lateral direction than the target area presented by the protective barrel, 2, of the FIG. 1 prior art. The FIG. 2-3 protective cap has a second, guide ramp surface, 14, with a overall outer dimension, 22, on the order of 3.5 cm., and a boss, 18, which has a lateral dimension on the order of 1.2 cm. Therefore, the second guide surface defines a lateral projection guard annulus with a width of 1.15 cm. It should be appreciated that while a protective cap having a second ramp surface and an axially extending flange, 6, to engage against a complementary surface of the protective barrel entrance guide extension is shown, any other shape of cap, with a dimension, 22, is consistent with the first embodiment of this invention. FIG. 2 illustrates that the needle hub, 4, is contained completely within the axial extent of the protective barrel, thereby enabling use of any cap which extends and seals against the extended opening of the entrance guide means.

Figure 4:
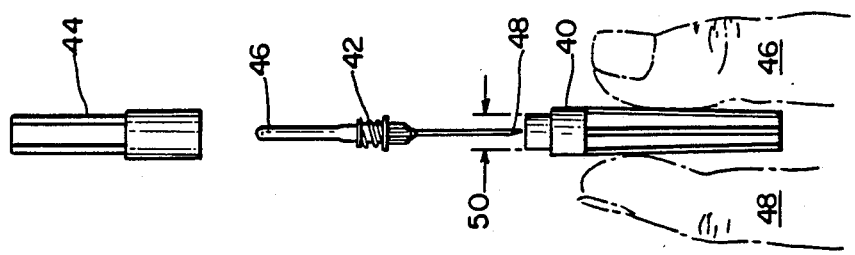
FIG. 4 is a vertical elevation explosion view of a second prior art device.

FIG. 4 represents a second common needle assembly as used in hospital and laboratories. FIG. 4 roughly represents a Venoject® which is sold by Terumo-Kaboshiki Kaisha, and particularly a multi-sample model 21GX1". Such multi-sample needles have a hub, 42, a first needle having a distal end, 48, and a second needle, 46, which is located within a surrounding rubber shield, as shown. A prior art protective barrel for such a double needle comprises an annular collar, 40, and a protective cap, 44. Conventionally, both cap and barrel are fluted to facilitate grasping, as by a forefinger, 48, and a thumb, 46. As in the prior art device of FIG. 1, the target for reinserting the tip, 48, is only the dimension, 50; which is substantially equal to the target for insertion of the cap, 44, over the second needle, 46.

Figure 6:
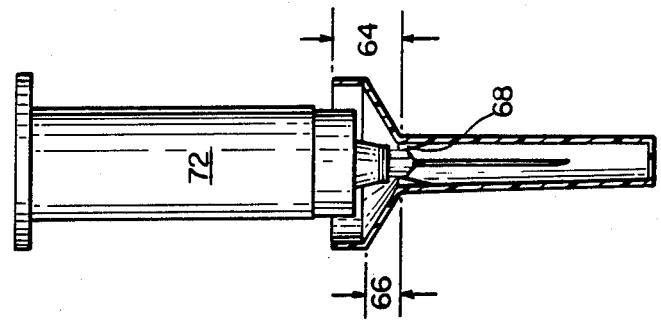
FIG. 6 is a vertical elevation view, in partial section showing a multi-sample tube in use with the second embodiment of the invention.
Figure 5:
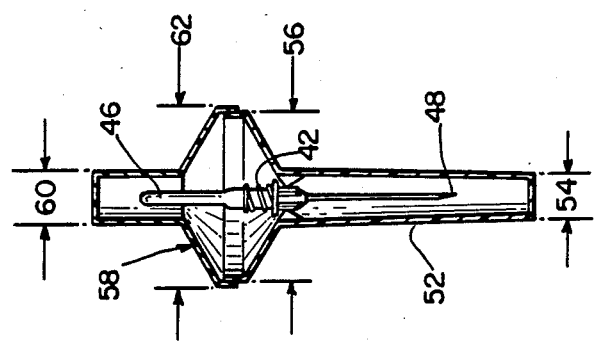
FIG. 5 is a vertical elevation view, in partial section, showing a second embodiment of the present invention.

FIGS. 5 and 6 represent a second, preferred embodiment protective packaging useful with such multi-sample needles, wherein a barrel, 52, axially extending to accommodate any given length needle mounted upon a threaded hub, 42, with a distal end, 48. The outer dimension of a barrel, 54, according to the present invention, also bears a relationship to the outer dimension of the axially and laterally extending entrance guide means, with an overall dimension, 56. The preferred relationship according to the second embodiment has a dimension 56 of approximately 3.0 cm., and an outer dimension for the barrel, (proximate its open upper end) of approximately 1 cm., thereby defining a width to the laterally projected annulus behind the obverse surface of the first ramp which is 1.0 cm. As shown in FIG. 5, the protective cap has an overall lateral dimension, 62, of 3.2 cm., and an axially extending boss with an overall lateral dimension of approximately 1.0 cm.; thereby defining a width to the laterally projected annulus behind the obverse surface of the second ramp which is 1.1 cm. The boss in this second embodiment preferably is hollow, to enable the tip of the second needle, 46, to be encased within the boss and extend towards a closed end of the cap. The second embodiment cap, 58, of course is usable with the first embodiment. For both first and second embodiments, the angle between an interior ramp surface and the centerline of the device is greater than 45 degrees, and preferably between 50 and 80 degrees. This range ensures both a significant finger guard dimension around either cap or barrel, and also a sufficient clearance proximate the hub of the needle, to enable a direct manipulative grasping, as necessary.

In FIG. 6 the double needle hub has been attached to a multi-sample blood collection tube holder, 72. Here again, the needle hub frictionally is engaged against any type of threads or frictional surface, 68, and the axial extent of the ramp, 66, bears a relationship to the overall lateral dimension, 56, which will ensure access for either fingers, or the significant width of a multi-sample tube holder. The multi-sample tube holder illustrated in FIG. 6 roughly represents a Tefumo Venoject® holder, as available from Terumo-Kabushki Kaisha. Similar multi-sample tube holders also are available from Becton, Dickenson under the brand, Vacutainer ®.

FIG. 7 represents a third, prior art device for which the present invention predicates improvement. FIG. 7 roughly represents, in vertical elevation view and partial section, a Monoject ® syringe, as available from Sherwood Medical Company, which is disposable and designated in its protective cap as a 3 cc., 23GX1". The protective packaging for such a prior art syringe and needle assembly comprises a protective barrel, 74, an axially extending, right-circular cylinder extension housing, 80, with an upper end having a removable cap element, 82. The proximate end of the housing, 80, includes an inwardly extending flange, 86, which engages against an outer surface of the needle hub, 78, so as to provide a sterile seal. The needle hub, 78, frictionally engages about a tapered cylinder, 88, and has a flange which rests upon the open end of the barrel, 74.

FIG. 8 represents a third embodiment of the present invention where the packaging is in combination with the same syringe, 76, illustrated in FIG. 7. The protective barrel has a lateral dimension, 90, and an entrance guide means having a lateral dimension illustrated at 92. The housing extension, 100, has, at its proximate end, an inwardly directed flange, 48, which partially extends over the inclined surface which is obverse to the entrance guide means, 94, as illustrated. The resulting seal both protects sterility within the enclosure, and prevents further forward motion of the barrel, out the proximate end of the housing, 100. The distal end of the housing, 100, includes a conventional form of cap, 104, which engages about the outer surface of the extending housing. The cap, 104, substantially is equivalent in shape and function to the prior art cap, 82, illustrated in FIG. 7. In the preferred third embodiment of FIGS. 8 and 10, the lateral dimension of the entrance guide means, 102, is approximately 2.8 cm. and the lateral dimension of the barrel proximate its open end, 90, is approximately 1.1 cm.; creating a lateral projected annular defined behind the entrance ramp obverse surface, 94, which is 0.85 cm. The third embodiment ramp surface, 94, has also an angle to the greater centerline which is greater than 45 degrees, and substantially less than 90 degrees, with a preferred range being between 50 and 80 degrees.

In each of the three embodiments, the improved barrels end caps preferably are of a thin-wall construction, and an easily moldable, sterilizable plastic, such as polypropylene. While each of the three embodiments illustrate a needle having a length in the vicinity of 1-2 inches, as common for intravenous and intramuscular use, the principles of the present invention equally are applicable to needles of significantly greater axial length, for example, Lumbar puncture needles (on the order of 6 inches), and aspiration or biopsy needles to (on the order of 8-9 inches). The present invention requires only a relationship between the overall lateral width of the entrance target and the open end of the conventional barrel, so an annulus is defined about the finger holding zone on the outer surface of the barrel. The axial extent of the barrel is not critical, and may be any length required to accommodate a given needle.

The three embodiments ensure not only that a needle is protected and sterile by its factory-packaging, but also that replacement of the guard, will be with a higher degree of safety to the forefinger and thumbs of the manipulator than previously available. The present invention defines an inclined ramp surface both for the purpose of guiding a laterally misaligned needle as it is directed towards the open end of the barrel proper, and also to create guard of a sufficient width to act a protective annulus there behind. The invention ensures a most natural gripping position, whereby forward areas of the fingers will be protected. To illustrate the target which the user will experience in using a prior art device, such as FIG. 7, and a target according to the present invention, as shown at FIG. 8, applicant further points to FIGS. 9 and 10. FIG. 9 is a top plan view of the barrel from the embodiment of FIG. 7, after the protective barrel, 74, vertically has been moved, upwardly and outwardly of the disposable outer extending housing, 80. The embodiment of FIG. 7 comprises three parts; barrel, 74, extending housing, 80, the cap, 82. In use, the user taps the bottom of barrel, 74, to move the syringe, 76, and protective barrel, 74, (as an assembly), directly upward, through an opening provided by removing the top cap, 82. Once the syringe and needle have been used, the operator very likely will attempt to replace only the protective barrel, 74, but not the extending housing, 80. Laboratory and hospital experience suggests only the protective cap, 74, will remain to be replaced over the needle; the extending housing, 80, and cap, 82, usually are immediately disposed of. The present invention ensures that, even though the extending housing, and the cap, of FIG. 8 have been discarded, the structure of the protective barrel, 94, is sufficient to ensure that a reinsertion of the needle into the open end of the barrel is according to principles of the present invention. FIG. 9 illustrates that the width of the needle hub flange, 84, is on the same order as the interior, open dimension of the barrel, 74 and that a very small target area is presented with such forms of needle and guard assemblies. FIG. 10 represents a lateral top plan view of the third embodiment of FIG. 8, after the extending housing, 100, has been removed. A first guide ramp surface, 94, tremendously increases the available area for lateral misalignment, and the overall first guard means width, 102 (and a similar interior dimension, 92, between inner surface points on the small flange, 96), which facilitates the axial motion and sealing of the entrance guide means within the interior surface of the extending housing, 100, as the needle and syringe assembly first is removed from the protective housing, 100.

FIG. 11 represents a fourth embodiment of the invention, in that the FIG. 8 circular section, 96, is replaced by a segmented surface, to 104, to prevent rolling of the device on a horizontal surface, for example. The ramp surface, 106, may be joined to a short segmented flange, 104, and be circular or have transition elements, molded to accommodate an intersection with the segmented flange, 104. In any case, the segmented ramp, 106, allows for a transition into the open upper end, 108, of the protective barrel itself.

FIG. 12 represents a fifth embodiment of the present invention insofar as projecting ridges, 114, are provided on the exterior surface of a entrance guide means, 112, which has an interior dimension, 90, equivalent to that as shown in FIG. 10. The ridges, 114, are usable with any particular ramp surface, 110, and the function of the ridges primarily is to stop rotation of the device, when placed upon a horizontal surface. In any of FIGS. 8, 10, 11 and 12, the flange may have a very short axial extension, or be as tall as that shown for 96, in FIG. 8.

While five preferred embodiments of the present invention have been shown and described, it will be apparent to one of ordinary skill in this art that variations can be made, without departing from the spirit of the present invention. Accordingly, the present invention is to be defined by the scope of the appended claims, when read in light of the disclosure.

We claim:

1. In a protective barrel and cap packaging for enclosing a hypodermic needle, which is attached to hub at a proximate and extends axially to a distal end, wherein said packaging consists essentially of the combination of an axially extending protective barrel and a protective cap, wherein said barrel has an open end and a closed end, said open end being adapted to accept entry of a needle tip and frictionally engage about an outer surface of a needle hub, and said barrel closed end being adapted to surround a needle tip inserted therein, wherein further said protective cap has an open end and a closed end, said cap open end being adapted to engage with said barrel open end thereby to define an enclosure for any needle therewithin, the improvement comprising:

a needle entrance guide means attached to said barrel open end and extending laterally and axially therefrom to define a laterally enlarged barrel opening with a transition ramp surface into the barrel open end, and towards the barrel closed end to guide a laterally misaligned needle tip axially into said protective barrel open end, said ramp surface making an included angle with the axial centerline of said barrel which is greater than 45 degrees and defining an obverse ramp outer surface between said enlarged barrel opening and said barrel outer surface which has a lateral projected width greater than 0.5 cm. and wherein a laterally enlarged cap open end is defined to engage with said laterally enlarged barrel opening, thereby to define said enclosure, whereby the obverse surface to said ramp surface encourages a user's fingers to locate behind the ramp and around a barrel outer surface which is proximate the barrel open end.

2. The improved packaging according to claim 1, wherein said entrance guide means is circular in lateral section, said ramp surface is funnel-shaped.

3. The improved packaging according to claim 1, wherein said barrel and entrance guide means are thin-walled structures and a laterally extending first annulus is defined around the outer surface of the barrel by the entrance guide means outer surface, which is obverse to said ramp surface, said annulus having a lateral, projected width between 0.5 cm. and 1.5 cm.

4. The improved packaging of claim 3, wherein the lateral projected width of said first annulus is approximately 1.0 cm.- said barrel end entrance guide means are formed in one piece, of molded plastic, and said ramp surface and the centerline of the barrel form an angle of between 50 degrees and 80 degrees.

5. The improved packaging of claim 3 wherein said protective cap further comprises an axially extending housing having a proximate end adapted to engage partially around the barrel entrance guide means outer surface and enable said barrel closed end to be inserted through the housing distal end and come to rest by a sealing arrangement between the housing proximate end and the barrel entrance guide means outer surface, wherein further the closed end of said protective cap comprises a removable element that sealingly engages with the housing distal end to enable a needle and attached syringe assembly removably to be enclosed within said packaging.

6. The improved packaging of claim 5, wherein said entrance guide means is circular, said barrel ramp surface is funnel-shaped, and said axially extending housing is substantially a right-circular cylinder with a radically inward disposed flange at its proximate end that is adapted couplementally to seal against said first annulus portion of said entrance guide means outer surface.

7. The improved packaging of claim 6 wherein said entrance guide means has a proximate end attached to the barrel open end, and a distal end which comprises a laterally disposed, circular flange, axially extending from said ramp surface, and said housing proximate end further has an inner surface of said right circular cylinder which sealingly engages against the outer surface of said circular flange.

8. The improved packaging of claim 6, wherein said entrance guide means defines a polygon in lateral section and said ramp surface is funnel-shaped.

9. The improved packaging of claim 6, wherein the lateral projected width of said first annulus is approximately 1.0 cm., said extending housing is thin-walled and of plastic, and said ramp surface and the centerline of the barrel form an angle of between 50 degrees and 80 degrees.

10. The improved packaging of claim 6, wherein said protective cap removable element is circular, engages about the outer surface of said housing distal end, and has axially disposed ridges on its circumference to facilitate finger gripping and removal of said element from said housing.

11. The improved packaging of claim 1, wherein said entrance guide means is funnel-shaped with a proximate end attached to the barrel open end and a distal end which comprises a flange extending axially from said ramp surface, and said protective cap enlarged open end is adapted to engage around said flange.

12. The improved packaging according to claim 1, wherein said protective cap comprises a second guide means to facilitate placing said cap over a needle within said barrel, said second guide means comprising a second ramp surface which makes an included angle with the axial centerline that is greater than 45 degrees and extends from said cap enlarged open end axially and laterally inward along the interior of said cap towards said closed end.

13. The improved packaging according to claim 12 wherein said cap further comprises an axially aligned boss extending from the cap outer surface, wherein a second annulus is defined around the outer surface of said boss by a cap outer surface which is obverse to said second ramp surface, said second annulus having a lateral, projected width between 0.5 cm. and 1.5 cm.

14. The improved packaging of claim 13, wherein the lateral, projected width of said second annulus is approximately 1.0 cm., said cap and second guide means are of a one-piece, thin-wall construction and said boss is circular and has external ridges about its circumference, to facilitate finger gripping and removal of said ca from said barrel.

* * * * *